United States Patent
Forsell

(10) Patent No.: US 10,390,988 B2
(45) Date of Patent: Aug. 27, 2019

(54) ABSORBING SEALING DEVICE FOR AN INTESTINAL STOMA

(76) Inventor: Peter Forsell, Bouveret (CH)

( * ) Notice: Subject to any disclaimer, the term of this patent is extended or adjusted under 35 U.S.C. 154(b) by 409 days.

(21) Appl. No.: 13/384,099

(22) PCT Filed: Jul. 19, 2010

(86) PCT No.: PCT/SE2010/050860
§ 371 (c)(1),
(2), (4) Date: Jan. 13, 2012

(87) PCT Pub. No.: WO2011/008166
PCT Pub. Date: Jan. 20, 2011

(65) Prior Publication Data
US 2012/0123379 A1 May 17, 2012

Related U.S. Application Data

(60) Provisional application No. 61/213,812, filed on Jul. 17, 2009.

(30) Foreign Application Priority Data

Jul. 17, 2009 (SE) ...................................... 0900999

(51) Int. Cl.
*A61F 5/44* (2006.01)
*A61F 5/445* (2006.01)
(52) U.S. Cl.
CPC ............ *A61F 5/445* (2013.01); *A61F 5/4401* (2013.01); *A61F 2005/4402* (2013.01)
(58) Field of Classification Search
CPC ... A61F 5/44; A61F 5/4402; A61F 2005/4402
(Continued)

(56) References Cited

U.S. PATENT DOCUMENTS

| 4,187,850 A | 2/1980 | Gust |
| 4,210,132 A | 7/1980 | Perlin |

(Continued)

FOREIGN PATENT DOCUMENTS

| EP | 1700588 A1 | 9/2006 |
| WO | WO 96/32904 | 10/1996 |
| WO | WO 2008/124715 | 10/2008 |

OTHER PUBLICATIONS

International Search Report for PCT/SE2010/050860, dated Oct. 19, 2010.

*Primary Examiner* — Jacqueline F Stephens

(57) ABSTRACT

The invention discloses an ostomy accessory (20) for an intestinal stoma of a mammal ostomy patient, adapted to be used together with an implanted constriction device with an artificial closing sphincter function for closing the intestinal passageway. The ostomy accessory is adapted to absorb secret from the mucosa wall of the part of the intestine which is distal to the constriction device, which may secrete or disseminate some liquid matter, which may thus spill out and cause discomfort to the patient, for example by staining the clothes of the patient. The ostomy accessory comprises an insertion portion (21) for insertion into said intestinal stoma and comprising an absorbing body (23, 24, 25) for absorbing and retaining liquid matter consisting of liquid secreted from a mucosa wall of the intestine (31). The accessory (20) also comprises an outer part (22) attached to the insertion portion and adapted to seal said stoma (5) together with the insertion portion (21), the outer part (22) comprising a liquid non-permeable layer in order to allow the absorbing body to retain absorbed liquid secretions from the mucosa wall so that the mucosa wall does not dehydrate.

16 Claims, 4 Drawing Sheets

(58) Field of Classification Search
USPC .................................. 604/361, 33; 424/423
See application file for complete search history.

(56) References Cited

U.S. PATENT DOCUMENTS 4,258,704 A    3/1981   Hill
4,781,176 A *  11/1988  Ravo ..................... A61F 2/0009
                                                         600/30
5,045,052 A    9/1991   Sans

* cited by examiner

ABSORBING SEALING DEVICE FOR AN INTESTINAL STOMA

This application is the U.S. national phase of International Application No. PCT/SE2010/050860, filed 19 Jul. 2010, which designated the U.S. and claims priority to Swedish Application No. 0900999-4, filed 17 Jul. 2009; and claims the benefit of U.S. Provisional Application No. 61/213,812, filed 17 Jul. 2009, the entire contents of each of which are hereby incorporated by reference.

TECHNICAL FIELD

The present invention discloses an ostomy accessory for an intestinal stoma with an artificial closing sphincter function.

BACKGROUND

In anatomy, a natural stoma is an opening in the body, with the opening out from the body, such as the mouth; essentially any hollow body organ can be surgically manipulated into a stoma, if and as necessary. Examples of such organs are the esophagus, stomach, duodenum, ileum, colon, pleural cavity, ureters, and kidney pelvis.

One well-known form of a stoma is a colostomy, which is a surgically-created opening in abdominal wall where the large intestine exits. A colostomy allows the removal of feces out of the body, bypassing the rectum, and to drain into a pouch or other collection device.

A stoma, as explained above, refers to a mouth-like part or opening, and in particular, it can refer to a surgical procedure involving the gastrointestinal tract, the GIT, or the gastrointestinal system, the GIS. The GIT begins at the mouth or oral cavity and continues until its termination, which is the anus. Such a surgical procedure is usually undertaken as a result of, and as a solution to, a disease in the GIT. The procedure involves dissecting the GIT or the GIS, usually between the later stage of the small intestine, the ileum, and the large intestine or colon, hence the term "colostomy", and exiting it from the body in the abdominal region.

The point of exit is then a surgically created stoma. In order to minimize negative effects, it is preferable to perform this procedure as far down in the tract as possible, as this allows the optimal amount of natural digestion to occur before removing digested food as faecal matter from the body.

Traditionally, the stoma is usually covered with a removable pouching system (attached by means of an adhesive or by mechanical means) that collects and contains the output for later disposal. Modern pouching systems enable most individuals to resume reasonably normal activities and lifestyles after surgery. However, traditional pouching systems still cause a patient some degree of discomfort.

A novel ostomy procedure exists that improves the comfort of the patient by means of implanting an artificial constriction device at a point in the GIT or the GIS. The constriction device can then be operated to open at a point in time which is chosen by the patient or, by, for example, medical personnel, and faecal matter can thus be removed at a point in time which is chosen by the patient or the medical personnel. However, following this novel procedure, the patient will still be left with an stoma on the abdomen. This stoma may exhibit some transpiration or dissemination through the intestinal wall or leakage, mainly of fluid matter from the mucosa wall of the intestine, which has been the subject of the ostomy procedure.

SUMMARY

It is an object of the present invention to further improve the comfort of a patient who has been through the novel ostomy procedure described above. As mentioned, the novel ostomy procedure will still leave the patient with a stoma, which may exhibit some dissemination of fluid through the intestinal wall, which may be a problem for the patient.

This problem is addressed by the present invention in that it discloses an ostomy accessory for an intestinal stoma of a mammal ostomy patient with an artificial closing sphincter function which normally is closed, preferably by an implanted constriction device, e.g. by an implanted constriction device of the novel procedure as describe above.

The ostomy accessory of the invention comprises an insertion portion for insertion into the intestinal stoma, and the insertion portion comprises an absorbing body for absorbing and retaining liquid matter secreted from a mucosa wall of the intestine.

The inventive ostomy accessory also comprises an outer part attached to the insertion portion, adapted to seal the stoma together with the insertion portion. The outer part of the accessory comprises a liquid non-permeable layer, in order to allow the absorbing body of the accessory to retain absorbed liquid secretions from the mucosa wall of the intestine, so that the mucosa wall does not dehydrate.

Hence, by means of the ostomy accessory of the present invention, a patient who has been through an ostomy procedure which implants a constriction device, for example on the GIT or the GIS, can "seal" the stoma, in order to, for example, protect his or her clothes, whilst still protecting the mucosa wall of the intestine from dehydrating.

To summarize there is provided an ostomy accessory adapted to be used together with an implanted constriction device with an artificial closing sphincter function for closing the intestinal passageway, wherein said ostomy accessory is adapted to absorb secretions from the mucosa wall of the part of the intestine which is distal to the constriction device, which may secrete or disseminate some liquid matter, which may thus spill out and cause discomfort to the patient, for example by staining the clothes of the patient, the accessory comprising an insertion portion for insertion into said intestinal stoma, said insertion portion comprising an absorbing body for absorbing and retaining liquid matter, consisting of liquid secreted from a mucosa wall of the intestine, the accessory also comprising an outer part attached to the insertion portion and adapted to seal said stoma together with the insertion portion, the outer part comprising a liquid non-permeable layer in order to allow the absorbing body to retain absorbed liquid secretions from the mucosa wall so that the mucosa wall does not dehydrate.

In one embodiment, in order to retain the accessory of the invention in place, the insertion portion of the accessory is shaped after the dimensions of the stoma, so that the accessory is retained in the stoma by means of mechanical contact between the insertion portion and the stoma.

In other or complementary embodiments, the accessory of the invention is kept in place by means of an attachment layer comprised in the outer part of the accessory for attachment to the outside abdominal wall of the mammal patient. This attachment layer can be adapted to, for example, create a surface tension between the outer part and the abdominal wall, in order to retain the outer part of the inventive accessory against the abdominal wall. Also, in some embodiments, the attachment layer can comprise an adhesive material or a layer of such a material.

According to a special embodiment, ostomy accessory according to the invention comprises a gasket sealingly extending around its insertion portion in order to further seal the stoma and to prevent leakage of body fluids.

The gasket may comprise a first inner skin contacting layer, an second outer layer; and at least one intermediate layer capable of absorbing body fluids from the stoma, wherein at least said inner layer admits body fluid passage to said intermediate layer. The gasket preferably is essentially ring shaped and the first and second layers are joined in an annular seal.

In an alternative embodiment cling wrap eller cling film may be used as a skin contacting layer. The original plastic wrap (Saran®) was made of PVC, but due to the risk of transfer of plastisizers into food, LDPE (low density polyethylene) is preferable.

For general use, an almost unlimited number of polymer films are available. These can be obtained in many different varieties, as clear, opaque, matte, glossy, colored or colorless, uncoated or coated (e.g. with a metal layer, preferably gold for surgical applications), and in different gauge (thickness), elasticity etc.

Polymer films have also been developed for particular medical and surgical applications, such as wound closure, prolonged release of drugs (medical patches), sealing and reinforcing against air leakage in thoracic surgery and against leakage of low pressure or oozing bleeding or fluid leakage following surgical procedures on soft tissue, dura replacement, i.e. to seal and reinforce against fluid (including cerebrospinal fluid (CSF)) and/or blood leakage where repair of the dura mater is required.

For surgical applications, the polymer film is preferably absorbable.

BRIEF DESCRIPTION OF THE DRAWINGS

The invention will be described in more detail in the following, with reference to the appended drawings, in which.

DETAILED DESCRIPTION

Figure 1:
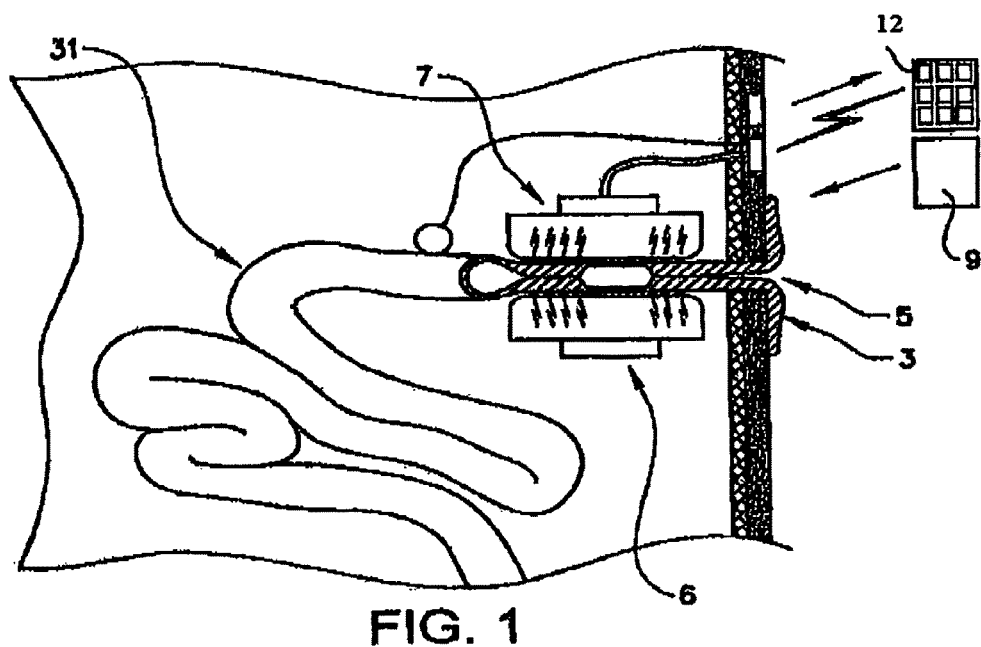
FIGS. 1 and 2 show an intestinal stoma and its immediate surroundings.

In order to explain the background of the present invention, FIG. 1 shows a cross section of a part of the abdomen of a mammal patient who has been through the novel ostomy procedure described above. As can be seen in FIG. 1, the novel procedure, in similarity to traditional ostomy procedures, involves making an opening in an intestine 31 of a patient, as well as creating an opening in the abdomen of the patient, out of which opening a stoma 5 is surgically created for the intestine 31.

As can be seen in FIG. 1, following the procedure, parts 3, of the intestine 31 are suitably attached to the outside of the abdomen in order to assist in creating the intestinal stoma 5. This is primarily similar to a traditional ostomy procedure. However, as opposed to traditional ostomy procedures, the novel procedure comprises arranging a constriction device in the abdomen of the patient, with the constriction device being able to open or close access between the intestine 31 and the surgically created stoma. As shown schematically in FIG. 1, the constriction device may for example comprise first 6 and second 7 constriction parts, which cooperate to cause the intestine to constrict, thereby closing access between the intestine 31 and the stoma 5.

When and as needed, the patient or, for example, medical personnel attending to the person may cause the constriction device to open, i.e. to cause the first 6 and second 7 constriction parts to distance themselves from each other, so that there is essentially free passage between the intestine 31 and the stoma 5; the constriction device can also be made to close. The operation of the constriction device can, for example, be carried out by means of a wireless remote control 12. The constriction device system may also be wirelessly recharged by a power supply and feedback receiving unit 9.

In order to enable a patient who has been through the novel procedure to live without a pouch on the outside of their abdomen, the novel procedure may also comprise arranging a reservoir for faecal matter inside the patient's abdomen.

Such a reservoir can be made either from the patient's own intestine, or by implanting an artificial reservoir before the constriction device. Such a reservoir can then be accessed and emptied at a point in time which is convenient.

Figure 2:
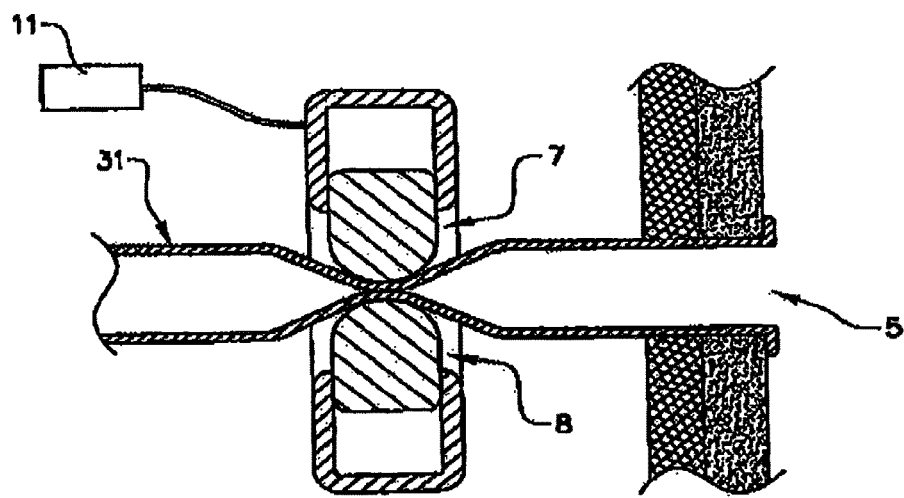

FIG. 2 schematically shows the constriction parts 7, 8 of a constriction device, together with a control unit 11 for the constriction device. In FIG. 2, the intestinal stoma or opening 5 is also shown schematically.

Thus, the faecal matter from the patient is more or less entirely collected in the artificial reservoir "inside" the constriction caused by the constriction device 6, 7, and will not leak into the stoma 5. However, the mucosa wall of the part of the intestine 31 which is distal to the constriction device may still secrete or disseminate some liquid matter, which may thus spill out and cause discomfort to the patient, for example by staining the clothes of the patient.

Figure 3A:
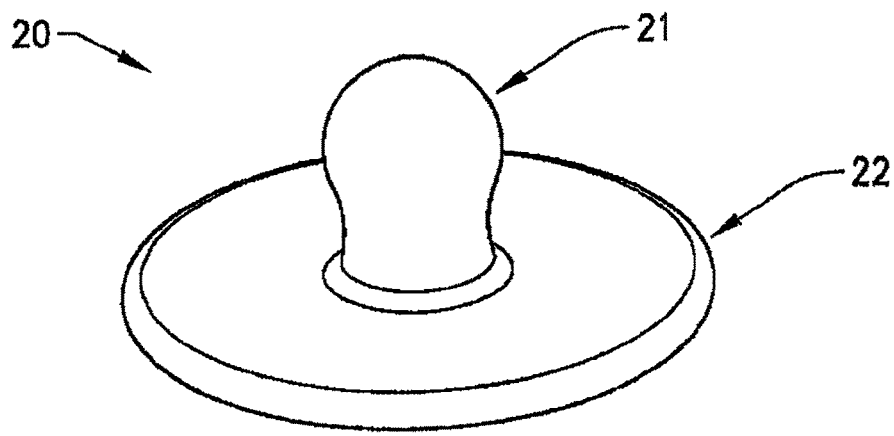
FIGS. 3-5 show exemplary embodiments of an ostomy accessory of the invention in different views.
Figure 3B:
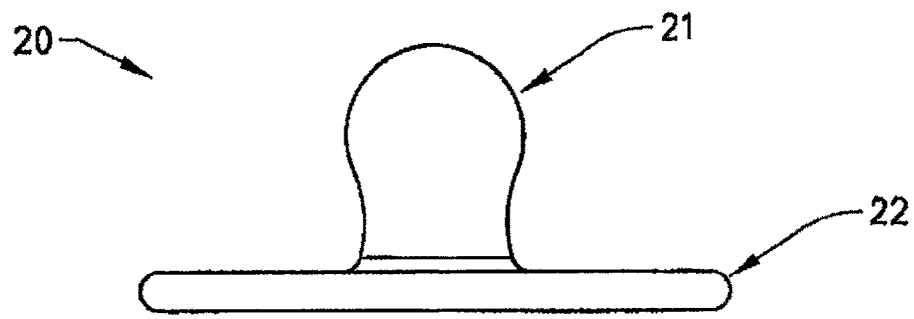
Figure 3C:
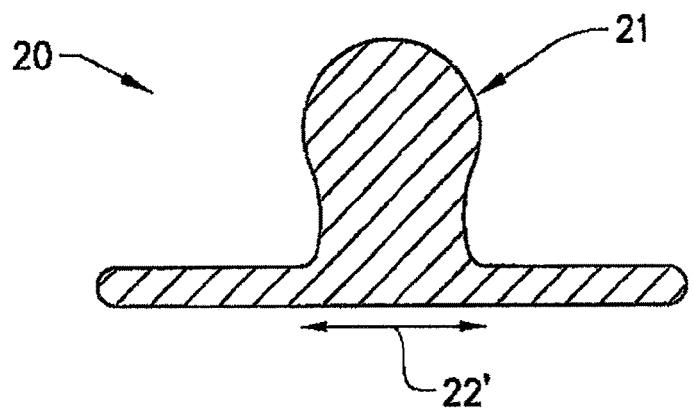

In order to address the problem of liquid matter of the kind described above, the present invention discloses an ostomy accessory 20, one embodiment of which is shown in different view in FIGS. 3a-3c: as shown in FIG. 3a, the ostomy accessory 20 of the invention comprises an insertion portion 21 for insertion into an artificial stoma such as the one 5 shown in FIGS. 1 and 2. The ostomy accessory 20 of the invention also comprises an outer part 22 which is attached to the insertion portion and is adapted to seal the stoma 5 together with the insertion portion 21. FIG. 3b shows the ostomy accessory 20 of the invention in a side view.

Suitably, the insertion portion 21 is attached to the outer part 22 so that a portion 22' of the outer part 22 forms an outer wall of the insertion portion 22, as shown in the side view of FIG. 3c.

In order to absorb and retain liquid matter secreted from a mucosa wall of the intestine, the insertion portion 21 comprises an absorbing body, whilst the outer part 22 of the inventive accessory 20 comprises a layer which is liquid non-permeable, in order to allow the absorbing body and the insertion portion to retain absorbed liquid secretions from the mucosa wall so that the mucosa wall does not dehydrate. This illustrates another function of the ostomy accessory of the invention: secretions from the mucosa wall of the intestine should not spill out from the stoma; in addition, the insertion portion, with the aid of its absorbing body should retain such secretions, so that the mucosa wall of the intestine does not dehydrate.

Figure 4:
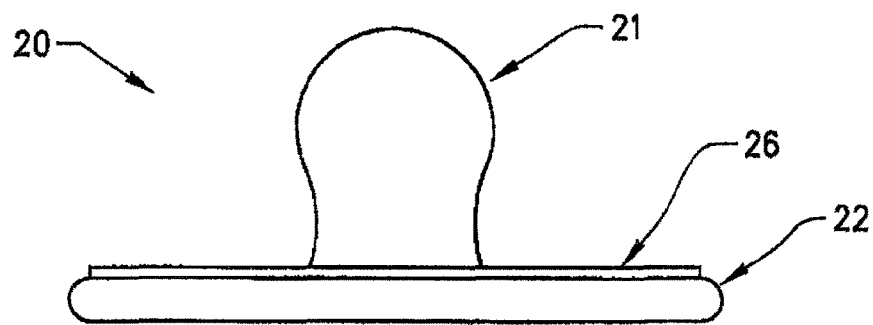

More will be said about the properties of the absorbing body as such later in this text, but first some alternative ways of retaining the inventive ostomy accessory 20 in place in the stoma and against the abdominal wall of the patient will be described with reference to FIG. 4.

In one embodiment, the insertion portion 21 of the ostomy accessory 20 is shaped after the dimensions of the stoma 5, so that the accessory 20 is retained in the stoma by means of mechanical contact between the insertion portion 21 and the stoma 5. In this embodiment, the surgical procedure as such will thus suitably create a stoma of "standard dimensions" and the insertion portion 21 can be given a corresponding standard size. Naturally, the materials used for the insertion portion 21 of the accessory 20 should have a certain degree of flexibility, so that certain variations in the size of the stoma can be accepted.

In an alternative or complementary embodiment, the outer part 22 of the ostomy accessory 21 comprises an attachment layer 26 for attachment to the outside abdominal wall of the mammal patient.

The attachment layer 26 can be used for attachment to the outside abdominal wall of the mammal patient by means of giving it a number of different properties, such as, for example, letting the attachment layer comprise an adhesive material, i.e. a material which causes the attachment layer 26 and thus the outer part 22 of the accessory 20 to adhere to the outside abdominal wall. The adhesive layer 26 can comprise a material which is similar to glue, although used in such proportions that the accessory can be attached and removed easily and without causing harm or discomfort to the patient.

In an alternative or complementary embodiment, the attachment layer 26 comprises a non adhesive attachment material, i.e. a material which adheres to the abdominal wall without the use of glue or the like. One example of such a material is a material which causes a static electrical effect between the abdominal wall and the attachment layer 26, which in turn causes the attachment layer and thus the outer part of the accessory to adhere to the outside abdominal wall.

In one embodiment, the attachment layer 26 comprises a polymer film,

Another example of choice of material for a non adhesive attachment layer is a material which creates a surface tension between the outer part of the accessory and the abdominal wall, for retaining the outer part of the accessory against the outside abdominal wall.

One example of a non adhesive attachment layer is a layer of a thin plastic material with miniscule "ridges" and "valleys" on the surface of the material, which causes the surface of the material to cling to other surfaces, such as, for example, the abdominal wall of the mammal ostomy patient.

Returning now to the properties of the absorbing body of the insertion part 21, this will be described in more detail with reference to FIG. 5. The design and materials used for the absorbing body should be such that the absorbing body essentially retains its shape, whilst absorbing and retaining secreted liquids. In one embodiment, shown in FIG. 5, the absorbing body comprises an absorbing core 25, which is suitably manufactured from a fibre material in the form of natural or synthetic fibers with absorbent characteristics, or from a mixture of natural and synthetic fibers or other absorbent materials.

The absorbing core can also comprise a predetermined proportion, for example 40-60%, of a superabsorbent material, for example polymer materials in the form of particles, fibres, flakes or the like, which have the ability to absorb and chemically bind liquid in amounts which are equivalent to several times their own weight to form an aqueous gel.

Figure 5:
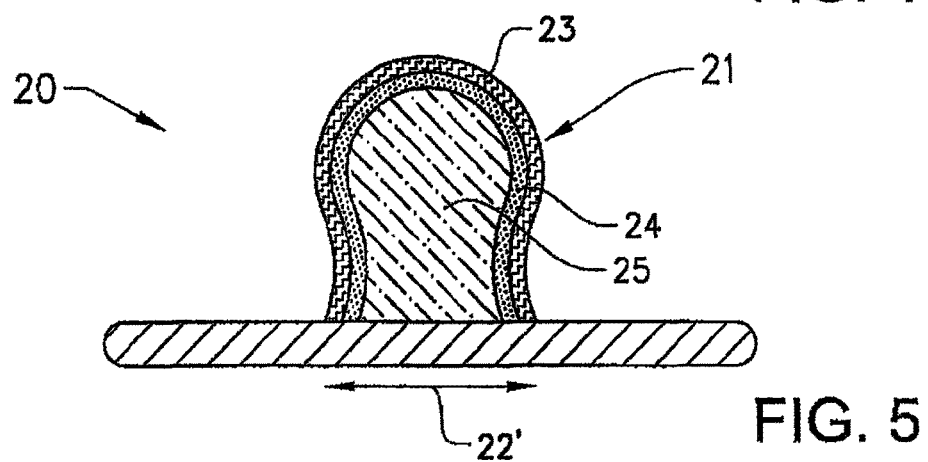

In one embodiment, included in FIG. 5, the absorbing body comprises, in addition to the absorbing core, an outer layer 23 of a liquid permeable material, in order to further allow it to retain its shape whilst absorbing liquids secretions. The layer of liquid permeable material preferably consists of a fibrous material, for example a soft nonwoven material, although it can also comprise other materials or material laminates. The liquid permeable layer is preferably fully or partially perforated, although in can also be entirely imperforate. Examples of suitable nonwoven materials are synthetic fibers such as polyethylene, polypropylene, polyester, nylon or the like. Mixtures of different types of fibers can also be used as the nonwoven material. However, the choice of material for the liquid permeable layer is not restricted to nonwoven materials; materials, such as for example films of thermoplastic materials can also be used.

In a further embodiment, the absorbing body comprises a further layer 24 of material which is a so called admission material (also sometimes referred to as an acquisition material), said layer 24 being positioned between the absorbing core 25 and the outer layer 23 of liquid permeable material, in order to add to the absorbing core's absorbing capabilities whilst helping it to retain its shape. The admission material 24 is suitably in the form of a wadding material, but it can also comprise or consist of other materials. For example, so called airlaid materials may be used, which are materials that are usually based on cellulose fibers. The admission material 24 can also comprise fibrous materials in order to give it a certain degree of rigidity.

The layer 24 of admission material is suitably a porous, elastic, relatively thick (as compared to the outer layer of liquid permeable material) layer of material, for example in the form of a fibrous wadding material, a carded fiber wadding, a tow material or some other kind of bulky and/or resilient fiber material with a high instantaneous liquid intake capacity that is capable of temporarily storing liquid before it is absorbed by the absorbing core. The admission material may also be a porous foam material.

Figure 6:
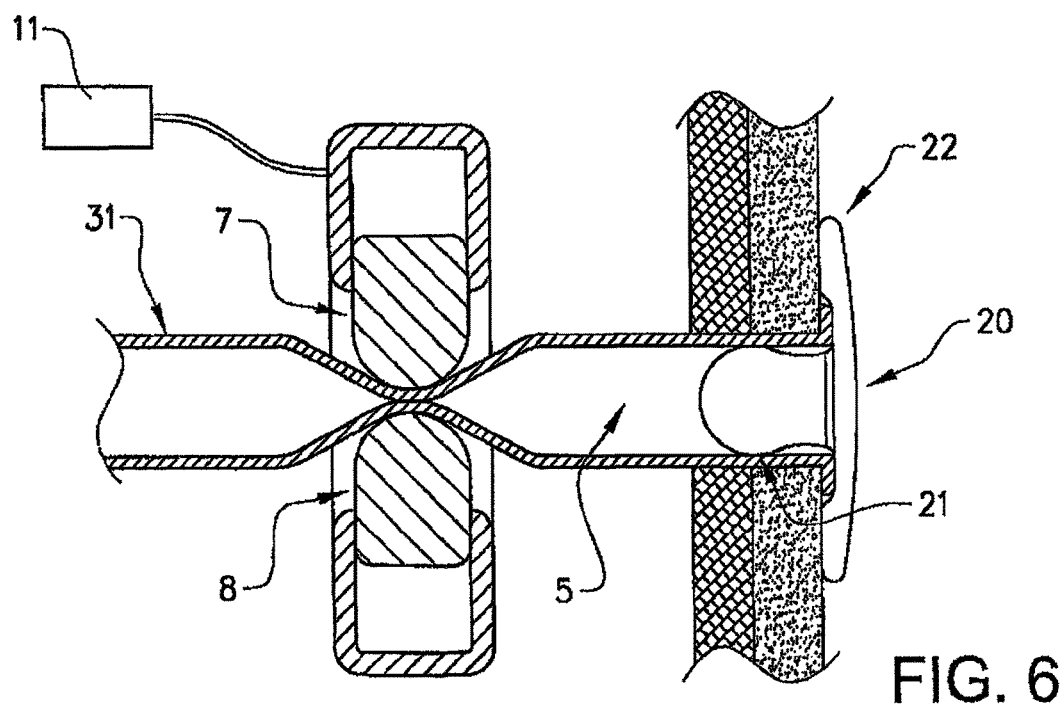
FIG. 6 shows an example of an ostomy accessory of the invention in use in an intestinal stoma.

FIG. 6 shows a side view of a mammal patient with the ostomy accessory 20 of the invention in use in a stoma 5 of the patient. As can be seen, the insertion portion 21 is inserted into the stoma 5, which is sealed by the insertion portion 21 together with the outer part 22.

Figure 7:
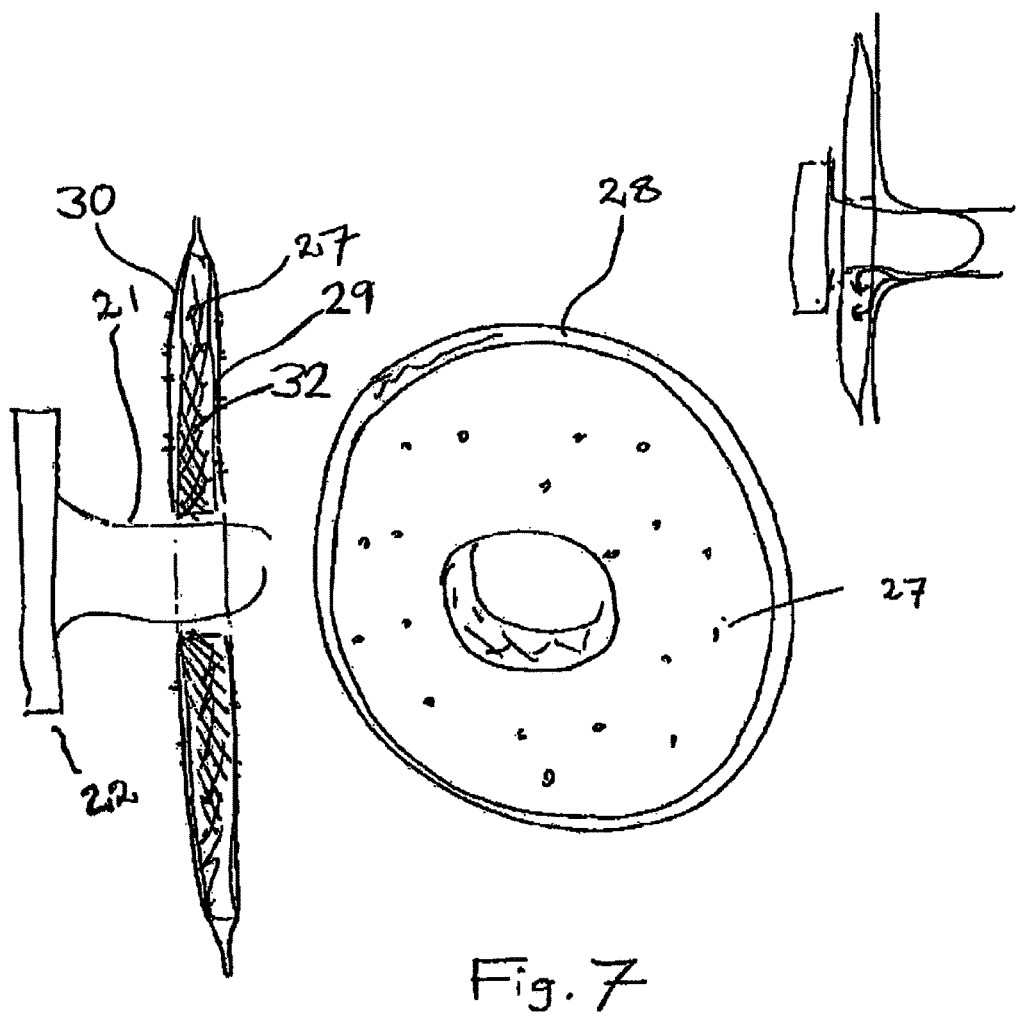
FIG. 7 shows an example of an ostomy accessory of the invention in use in an intestinal stoma.

FIG. 7 shows a special embodiment of ostomy accessory (20) according to having a gasket (27), sealingly extending around the insertion portion (21). The gasket will further seal the stoma and prevent leakage of body fluids. The gasket has a first inner skin contacting layer (29), and second outer layer (30); an intermediate layer (32) capable of absorbing body fluids from the stoma. The inner and/or outer layer is provided with openings that admit body fluid passage to said intermediate layer. As illustrated in FIG. 7, the gasket is ring shaped and the first and second layers are welded together to enclose the intermediate layer, which includes a body fluid absorbing tissue, for example according what has been outlined for the absorbing core in FIG. 5. The inner and outer layer preferably is made of biocompatible polyolefins, such as preferably LDPE or similar materials and can be made of materials that are suitably adhesive to the skin. The invention is not limited to the examples of embodiments described above and shown in the drawings, but may be freely varied within the scope of the appended claims.

The invention claimed is:

1. An ostomy accessory for an intestinal stoma of a mammal ostomy patient, adapted to be used together with an implanted constriction device with an artificial closing sphincter for independently from the ostomy accessory constricting the intestine from outside of the intestine for closing the intestinal passageway thereby hindering fecal matter to reach the ostomy accessory,
   wherein said ostomy accessory is adapted to work independently from the artificial closing sphincter and adapted to work in an intestinal environment where the artificial closing sphincter is preventing feces to reach the ostomy accessory, wherein said ostomy accessory is adapted to have its function consisting of to absorb non-fecal secret from the mucosa wall of the part of the intestine which is distal to the constriction device, the ostomy accessory comprising an insertion portion adapted for insertion into said intestinal stoma, said insertion portion comprising an absorbing body for absorbing and retaining liquid matter consisting of liquid secreted from a mucosa wall of the intestine, the accessory also comprising an outer part attached to the insertion portion and adapted to seal said stoma together with the insertion portion, the outer part being attached to a liquid non-permeable layer in order to allow the absorbing body to retain absorbed liquid secretions from the mucosa wall so that the mucosa wall does not dehydrate, and wherein said outer part is attached to an attachment layer adapted to create an electrostatic field between the outer part and the abdominal wall, adapted for retaining the outer part against the abdominal wall when non-fecal secret only is absorbed from the intestinal wall, wherein the insertion portion is attached to the outer part so that a portion of the outer part forms an outer wall of the insertion portion, wherein the insertion portion and the outer part are formed in one piece, without previously-separate coupled together pieces.

2. The ostomy accessory of claim 1, in which the insertion portion is shaped after the dimensions of the stoma, so that the accessory is retained in the stoma by means of mechanical contact between the insertion portion and the stoma.

3. The ostomy accessory of any of claims 1-2, in which the outer part comprises an attachment layer for attachment to the outside abdominal wall of the mammal patient.

4. The ostomy accessory of claim 3, in which said attachment layer comprises an adhesive material.

5. The ostomy accessory of claim 3, in which said attachment layer comprises a non-adhesive attachment material.

6. The ostomy accessory of claim 5, in which said non adhesive material comprises a material which causes a static electrical effect between the skin and the attachment layer.

7. The ostomy accessory of claim 5, in which said non adhesive layer is adapted to create a surface tension between the outer part and the abdominal wall, for retaining the outer part against the abdominal wall.

8. The ostomy accessory of claim 5, in which said non adhesive layer comprises a material which causes a static electrical effect between the skin and the attachment layer and which is also adapted to create a surface tension between the outer part and the abdominal wall, for retaining the outer part against the abdominal wall.

9. The ostomy accessory of claim 7 or 8, wherein said non adhesive layer comprises miniscule ridges and valleys on the surface of the material.

10. The ostomy accessory according to claim 5, wherein the attachment layer comprises a polymer film.

11. The ostomy accessory of any of the previous claims, in which the insertion portion also comprises a layer of a liquid permeable material arranged as an outer layer for the absorbing body.

12. The ostomy accessory of claim 11, in which the insertion portion also comprises a layer of a subjacent admission material arranged between the outer layer and the absorbing body.

13. The ostomy accessory according to claim 1 comprising a gasket, sealingly extending around the insertion portion in order to further seal the stoma and to prevent leakage of body fluids.

14. The ostomy accessory according to claim 13, wherein the gasket
    comprises a first inner skin contacting layer, an second outer layer; and at least one intermediate layer capable of absorbing body fluids from the stoma, wherein at least said inner layer admits body fluid passage to said intermediate layer.

15. The ostomy accessory according to claim 13 or 14, wherein the gasket is essentially ring shaped; and wherein first and second layers are joined in an annular seal.

16. The ostomy accessory according to claim 1 further comprising a gasket sealingly extending around and being configured to, when in use, be in contact with the insertion portion in order to further seal the stoma and to prevent leakage of body fluids.

* * * * *